(12) United States Patent
Gore et al.

(10) Patent No.: US 6,210,696 B1
(45) Date of Patent: *Apr. 3, 2001

(54) STABLE PESTICIDE DISPERSIONS

(75) Inventors: Robert Howard Gore, Southampton; Richard David Houghton, Harleysville; Warren Harvey Machleder, Blue Bell; William Dean Mathis, Doylestown; Luong Tu Nguyen, Lansdale; Bridget Marie Stevens, Horsham; Yan Sun, Dresher, all of PA (US)

(73) Assignee: Rohm and Haas Company, Phila, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/066,917

(22) Filed: Apr. 27, 1998

(51) Int. Cl.⁷ ............................. A01N 25/02; A01N 25/10

(52) U.S. Cl. ..................... 424/405; 424/407; 424/409
(58) Field of Search ........................ 424/405, 407, 424/409

(56) References Cited

U.S. PATENT DOCUMENTS

| | | | |
|---|---|---|---|
| 3,030,303 | 4/1962 | Ryan | 252/33.6 |
| 3,131,119 | * 4/1964 | Fordyce et al. | 514/483 |
| 3,773,926 | 11/1973 | Knowles et al. | 424/78 |
| 5,599,768 | 2/1997 | Hermansky | 504/116 |
| 5,674,514 | * 10/1997 | Hasslin | 424/405 |
| 5,753,248 | 5/1998 | Bott | 424/405 |
| 6,146,652 | * 11/2000 | Gore et al. | 424/405 |

* cited by examiner

*Primary Examiner*—Robert H. Harrison
(74) *Attorney, Agent, or Firm*—Ronald D. Bakule; Thomas D. Rogerson

(57) ABSTRACT

Stable dispersions of certain pesticides in agricultural oil are provided. In particular, the dispersions include a particulate pesticide, agricultural oil, and an agricultural oil-soluble polymer, the polymer in some instances containing a copolymerized polar monomer. Also provided is a method for forming the stable dispersion.

8 Claims, No Drawings

STABLE PESTICIDE DISPERSIONS

The present invention relates to a stable dispersion of a pesticide in an agricultural oil and a method for forming the dispersion. In particular the invention relates to a stable dispersion of a pesticide in an agricultural oil including: a pesticide having a particle size from 0.5–10 microns and selected from the group consisting of chlorinated nitrile, triazole, aralkyl triazole, triazole anilide, benzamide, alkyl benzamide, diphenyl ether, pyridine carboxylic acid, chloroaniline, organophosphate, phosphonic glycine salt, and mixtures thereof; an agricultural oil; and an agricultural oil-soluble polymer, the polymer having a weight average molecular weight from 3,000 to 120,000 and including 2.5–35% by weight of a copolymerized polar monomer. And the invention is related to a stable dispersion of a pesticide in an agricultural oil comprising: ethylene bisdithiocarbamate having a particle size from 2–10 microns; an agricultural oil; and an agricultural oil-soluble polymer, said polymer having a weight average molecular weight from 3,000 to 90,000 and including 0–35% by weight of a copolymerized polar monomer. The invention is also related to a method for forming the stable dispersion.

U.S. Pat. No. 3,773,926 discloses a method of and composition for the treatment of plants, the compositions containing certain pesticides dispersed in a conventional agricultural oil employing an N-vinyl-2-pyrrolidinone (4–15%)/alkyl methacrylate (85–96%) copolymer dispersant. The dispersant polymer is disclosed to have a average molecular weight of from about 300,000 to about 1,000,000.

U.S. Pat. No. 3,131,119 discloses compositions containing salts of dithiocarbamic acids such as ethylenebisdithiocarbamic acid and dimethyldithiocarbamic acid dispersed in oil using an organic solvent-soluble polymer which possesses a balance of hydrophilic and lipophilic groups. The lipophilic groups are supplied by hydrocarbon groups containing from 8–24 carbon atoms. The hydrophilic groups are supplied by multiple ether groups, carbonyl groups, carboxylic acid groups, carboxylic ester groups, amide groups, and amino groups. The organic solvent-soluble polymer is disclosed to have a molecular weight of about 100,000 to about 2,000,000.

There remains the need for stable dispersion of a variety of pesticides. We have now surprisingly found that a variety of stable dispersions can be made using agricultural oil-soluble polymers having a lower molecular weight than previously disclosed. These compositions facilitate making and storing of the dispersions, also considered as concentrates, even in hot climates, for their effective use in agronomic applications. Accordingly, the present invention provides a stable dispersion of certain pesticides in an agricultural oil and a method for forming the stable dispersion.

According to a first aspect of the present invention there is provided a stable dispersion of a pesticide in an agricultural oil comprising: a pesticide having a particle size from 0.5–10 microns and selected from the group consisting of chlorinated nitrile, triazole, aralkyl triazole, triazole anilide, benzamide, alkyl benzamide, diphenyl ether, pyridine carboxylic acid, chloroaniline, organophosphate, phosphonic glycine salt, and mixtures thereof; an agricultural oil, and an agricultural oil-soluble polymer, the polymer having a weight average molecular weight from 3,000 to 120,000 and including 2.5–35% by weight of a copolymerized polar monomer According to a second aspect of the present invention there is provided stable dispersion of a pesticide in an agricultural oil comprising: ethylene bisdithiocarbamate having a particle size from 2–10 microns; an agricultural oil; and an agricultural oil-soluble polymer, the polymer having a weight average molecular weight from 3,000 to 90,000 and including 0–35% by weight of a copolymerized polar monomer.

According to a third aspect of the present invention there is provided a method for forming a stable dispersion of a pesticide in an agricultural oil comprising admixing a pesticide selected from the group consisting of chlorinated nitrile, triazole, aralkyl triazole, triazole anilide, benzamide, alkyl benzamide, diphenyl ether, pyridine carboxylic acid, chloroaniline, organophosphate, phosphonic glycine salt; an agricultural oil; and an agricultural oil-soluble polymer, the polymer having a weight average molecular weight from 3,000 to 120,000 and including 2.5–35% by weight of a copolymerized polar monomer and mixing or shearing the admixture until the pesticide has a particle size from 0.5 to 10 microns.

According to a fourth aspect of the present invention there is provided a method for forming a stable dispersion of a pesticide in an agricultural oil comprising admixing ethylene bisdithiocarbamate; an agricultural oil; and an agricultural oil-soluble polymer, said polymer having a weight average molecular weight from 3,000 to 90,000 and including 0–35% by weight of a copolymerized polar monomer and mixing or shearing the admixture until the ethylene bisdithiocarbamate has a particle size from 2 to 10 microns.

By "stable dispersion of a pestcide in an agricultural oil" herein is meant a dispersion which did not gel during the dispersion process, i.e., a dispersion which did not gel, for example, in the homogenizer, bead mill, or ball mill used to mix and shear the admixture of the pesticide, the polymer, and the agricultural oil. The stable dispersion is stable relative to a dispersion of the same pesticide prepared in like manner in the absence of the polymer. Prefered are dispersions which, in addition meet the inital properties below. More prefered are dispersions which further meet the following properties after 1–2 weeks holding at 54 C. Typical desired values of the measured properties are given.

Initial Properties:

appearance=no gelling viscosity=less than 2000 cps, most preferably less than 1000 cps After 1–2 weeks at 54° C.:

appearance=no gelling viscosity=less than 2000 cps, most preferably less than 1000 cps % separation=top clear liquid; separation less than 10%.

sedimentation=sticky sediment on the bottom of jar; none.

By "particle size" herein is meant the volume average particle diameter as measured, for example by a laser particle size instrument such as the Coulter LS-130 particle sizer.

Pesticides herein include particulate agronomically effective fungicides, herbicides, and insecticides such as chlorinated nitrile, triazole, aralkyl triazole, triazole anilide, benzamide, alkyl benzamide, diphenyl ether, pyridine carboxylic acid, chloroaniline, organophosphate, phosphonic glycine salt, and mixtures thereof Also included are mixtures of the pesticides with other organic or inorganic agronomically active ingredients, for example, Dithane+Indar, Dithane+chlorothalonil, Dithane+cymoxanil, and Dithane+Copper Hydroxide. Examples of typical pesticides and their physical characteristics are presented in Table 1.

TABLE 1

Typical Pesticides used in this invention

| Trade Name | Action | Common Name | Family | Molecular Formula | Melting Pt ° C. | Sol. in H2O |
|---|---|---|---|---|---|---|
| Bravo | fungicide | Chlorothalonil | chlorinated nitrile | C8CL4N2 | 250–251 | 0.6–1.2 ppm |
| Dithane | fungicide | Mancozeb | ethylene bisthiocarbmate | C4H6MNN2S4x Zny | 192–204 | 6–20 ppm |
| Systhane | fungicide | Myclobutanil | triazole | C15H17ClN4 | 63–68 | 142 ppm |
| Indar | fungicide | Fenbunconazole | aralkyl triazole | C19H17ClN4 | 124–126 | 0.2 ppm |
| Pulsar | fungicide | Thifluzamide | | C13H6Br2F6N2OS | 178 | 1.6 ppm |
| RH-7281 | fungicide | n/a | alkyl benzamide | C14H16O2NCl3 | 167 | >1 ppm |
| Gallery | herbicide | Isoxaben | amide | C18H24N2O4 | 176–179 | 1–2 ppm |
| Kerb | herbicide | Pronamide | amide | C12H11CL2NO | 155–156 | 15 ppm |
| Visor | herbicide | Thiazopyr | pyridine carboxylic acid | C16H17O2N2SF5 | 79–81 | 2.5 ppm |
| Goal | herbicide | oxyfluorfen | diphenyl ether | C15H11ClF3NO4 | 85–90 | 0.1 ppm |
| Stam | herbicide | propanil | chloroaniline | C9H9Cl2NO | 91 | 130 ppm |
| Roundup | herbicide | glyphosate isopropyl ammonium salt | phosphonic glycine salt | C6H17N2O5PS | >200 | 40–50% |
| Imidan | insecticide | Phosmet | organophosphate | C11H12NO4PS2 | 72.0–72.7 | 25 ppm |

Notes: Dithane, Systhane, Indar, Pulsar, Kerb, Visor, Goal, and Stam are trademarks of Rohm and Haas Company. Bravo is a trademark of ISK Biosciences, Gallery is a trademark of Dow Elanco. Imidan is a trademark of Gowan Co. Roundup is a trademark of Monsanto Co. RH-7281 is a product of Rohm and Haas Company.

Typically the pesticides used in the stable dispersion and method for forming a stable dispersion of this invention were crystalline and had melting points greater than 50° C., molecular weights greater than 200, low solubility in paraffinic solvents, typically less than 1%, and contained polar functional groups such as, for example, ester, carbonyl, hydroxy, and cyano.

The agricultural oils used in the stable dispersions and method for forming a stable dispersion of this invention are oils suitable for agronomic application, typically of high purity, and generally composed of a single aliphatic chemical structure. They may be branched or linear in nature with typical carbon chain lengths of $C_{20}$ to $C_{26}$. They are characterized by low odor, low solvency for organic and organometallic compounds, low phytotoxicity to biological species, and low volatility. Commercial examples agricultural oil are: Orchex 796, Orchex 692, Sunspray 7N, Sunspray 11N, Oleo Branco, Isopar M, Isopar V, 100 Neutral, and Exxsol D-130. Other oils such as mineral oil; crop oil such as, for example, vegetable oil, peanut oil, and cottonseed oil; or synthetic may be acceptable Typical physical characteristics of agricultural oils are:

| | |
|---|---|
| Specific Gravity at 60/60° F. | 0.750 to 0.900 |
| Flash Point | >120° F. |
| Viscosity, SSU at 100° F. | 50 to 150 |
| Unsulfonated residue | >90% |
| Distillation range | 350° F. to 450° F. |

The agricultural oil-soluble polymers used in the stable dispersion and method for forming a stable dispersion of this invention typically are addition polymers formed from ethylenically unsaturated monomers. Prefered are copolymers of one or more monomers, the homopolymers of which are soluble in agricultural oils, and one or more polar monomers. More prefered are copolymers of one or more alkyl (meth)acrylates and one or more polar monomers.

Examples of the alkyl (meth)acrylates [alkyl(meth) acrylates is used herein to mean alkyl methacrylate or alkyl acrylate where the alkyl group contains from 1 to 15 carbon atoms are methyl methacrylate (MMA), methyl acrylate, ethyl acrylate, propyl methacrylate, butyl methacrylate (BMA) and acrylate (BA), isobutyl methacrylate (IBMA), hexyl and cyclohexyl methacrylate, cyclohexyl acrylate 2-ethylhexyl acrylate (EHA), 2-ethylhexyl methacrylate, octyl methacrylate, decyl methacrylate, isodecyl methacrylate (IDMA, based on branched ($C_{10}$)alkyl isomer mixture), undecyl methacrylate, dodecyl methacrylate (also known as lauryl methacrylate), tridecyl methacrylate, tetradecyl methacrylate (also known as myristyl methacrylate), pentadecyl methacrylate and combinations thereof Also useful are: dodecyl-pentadecyl methacrylate (DPMA), a mixture of linear and branched isomers of dodecyl, tridecyl, tetradecyl and pentadecyl methacrylates; and lauryl-myristyl methacrylate (LMA), a mixture of dodecyl and tetradecyl methacrylates. Examples of the alkyl (methacrylate) where the alkyl group contains from 16 to 24 carbon atoms are hexadecyl methacrylate, heptadecyl methacrylate, octadecyl methacrylate, nonadecyl methacrylate, eicosyl methacrylate, behenyl methacrylate(BehMA), and combinations thereof. Also useful are: cetyl-eicosyl methacrylate (CEMA), a mixture of hexadecyl, octadecyl and eicosyl methacrylate; and cetyl-stearyl methacrylate (SMA), a mixture of hexadecyl and octadecyl methacrylate.

The alkyl methacrylate and alkyl acrylate monomers described above are generally prepared by standard esterification procedures using technical grades of long chain aliphatic alcohols, and these commercially available alcohols are mixtures of alcohols of varying chain lengths containing between 10 and 15 or 16 and 20 carbon atoms in the alkyl group. Consequently, for the purposes of this invention, alkyl methacrylate is intended to include not only the individual alkyl methacrylate product named, but also to include mixtures of the alkyl methacrylates with a predominant amount of the particular alkyl methacrylate named. The use of these commercially available alcohols to prepare acrylate and methacrylate esters results in the LMA, DPMA, SMA and CEMA monomer mixtures described above.

The polar monomers may contain, for example hydroxy groups or Nitrogen-containing groups. The polar monomers preferably contain hydroxyl, carboxylic acid, basic nitrogen, or heterocyclic functionality. Examples of polar monomers are hydroxyalkyl(meth)acrylates such as hydroxypropyl methacrylate(HPMA), dialkylamino($C_1$–$C_8$)alkyl (meth) acrylates such as dimethylaminoethyl methacrylate (DMAEMA) and dialkylamino($C_1$–$C_8$)alkyl (meth) acrylamides such as dimethylaminopropyl methacrylamide (DMAPMAm), vinylpyridine, 2-methyl-5-vinylpyridine, 2-ethyl-5-vinylpyridine, 3-methyl-5-vinylpyridine, 2,3-dimethyl-5-vinylpyridine, 2-methyl-3-ethyl-5-vinylpyridine, methyl-substituted quinolines and isoquinolines, 1-vinylimidazole, 2-methyl-1-vinylimidazole (MVI), N-vinylcapro-lactam, N-vinylbutyrolactam and N-vinylpyrrolidone(NVP).

To achieve oil solubility in a typical agricultural oil, the alkyl side chains of the acrylate/methacrylate monomers should average at least about $C_7$–$C_9$. However, typically as the amount of the polar monomer in the polymer increases, the average chain length of the alkyl side chains in the (meth)acrylate comonomers must be increased, in order to maintain oil solubility. Therefore, a polymer that contains greater than 10% by weight of copolymerized DMAPMAm (basic nitrogen) or copolymerized HPMA (free hydroxyl) typically requires a greater amount of alkyl side chains containing $C_{16}$–$C_{18}$ alkyl rather than $C_7$–$C_9$ alkyl. Prefered are copolymers of $C_{12}$–$C_{20}$ methacrylates with 10–15% by weight of DMAPMAm. More prefered are coplymers of stearyl methacrylate(SMA) with 10–20% by weight of DMAPMAm.

The weight average molecular weight of the polymer, typically from 3,000 to 120,000 or from 3,000 to 90,000, depending on the pesticide to be dispersed, may also have an effect on the viscosity of the formulation, with higher molecular weight leading to higher solution viscosity. Higher solution viscosity may decrease particle mobility and thus delay separation and settling. However, higher solution viscosity may hinder the flowability, transfer, and facile dilution of the pesticide dispersion Prefered are weight average molecular weights of 15,000 to 90,000; more prefered are weight average molecular weights of 20,000 to 75,000.

The polymers are typically made by addition polymerization in agricultural oil, preferably by gradual addition free-radical polymerization of the monomers. The polymers are typically prepared by mixing the monomers in the presence of a polymerization initiator, agricultural oil and, optionally, a chain transfer agent. The reaction may be run under agitation in an inert atmosphere at a temperature of from about 60 to 140° C. and more preferably from 115 to 125° C. The reactions were typically run for about 4 to 10 hours or until the desired degree of polymerization hadbeen reached. As is recognized by those skilled in the art, the time and temperature of the reaction are dependent on the choice of initiator and can be varied accordingly. Polymers may be prepared by techniques known in the art to form graft polymers, block copolymers, star copolymers, or variable composition copolymers as well as random copolymers.

Initiators useful for this polymerization are any of the well known free-radical-producing compounds such as peroxy, hydroperoxy and azo initiators including acetyl peroxide, benzoyl peroxide, lauroyl peroxide, t-butyl peroxyisobutyrate, caproyl peroxide, cumene hydroperoxide, 1,1-di(t-butylperoxy)-3,3,5-tri-methylcyclohexane, azobisisobutyronitrile, 2,2'azobis(2-methylbutane nitrile), and t-butyl peroctoate. The initiator concentration is normally between 0.025 and 1% by weight based on the total weight of the monomers and more preferably from 0.05 to 0.25%. Chain transfer agents may also be added to the polymerization reaction to control the molecular weight of the polymer. The prefered chain transfer agents are alkyl mercaptans such as lauryl (dodecyl) mercaptan, and the concentration of chain transfer agent used is from about 0.1 to about 10% by weight.

The dispersion of a pesticide in agricultural oil was typically effected with pesticides which were either technical grade particulate pesticides("technicals") or formulated particulate pesticide compositions such as, for example, wettable powders and dispersible granules.

The technical grade particulate pesticides ranged in active ingredient content from 80 to 98% by weight and were solid at room temperature. The wettable powders and dispersible granules ranged in active ingredient content from 45% by weight to 75% by weight and had typical compositions as follows: 45 to 75% by weight pesticide; 20 to 50% by weight carrier; 2 to 10% by weight dispersant; and 2 to 10% by weight surfactant. The wettable powders and dispersible granules typically had been milled to an average particle size in the range of 2 to 10 microns.

The dispersions of this invention are typically applied in the field as dilutions into oil or oil/water/surfactant carriers. The spray tank mixtures may contain other formulated agronomic compositions such as, for example, surfactant adjuvants, emulsifiable concentrates, and wettable powders. Application may be made by ground or aerial spray equipment.

EXAMPLE 1

Preparation of agricultural oil-soluble polymer

Preparation of polymer 3. A 5 gallon reactor was fitted with a thermocouple, a temperature controller, a purge gas inlet, a water-cooled reflux condenser with purge gas outlet, a stirrer, and an addition tank. To the addition tank was charged 4911.59 grams of a monomer mixture of 4137.07 pbw stearyl methacrylate (96.5% purity), 704.52 pbw dimethylaminopropyl methacrylamide (100% purity), 40.00 pbw of a 50% solution of t-butyl peroctoate in mineral spirits (Lupersol PMS), 30.00 pbw dodecyl mercaptan. Sixty percent (2946.95 grams) of the monomer mixture in the addition tank and 736.74 grams of Orchex 796 oil were charged to the reactor which was then flushed with nitrogen for 30 minutes before applying heat to bring the contents of the reactor to 120° C. When the contents of the reactor reached 120° C., the balance of the monomer mixture in the addition tank was uniformly charged to the reactor over 90 minutes. At the end of the monomer mixture addition, the temperature in the reactor was lowered to 100° C. and 1124.21 grams of a feed consisting of 314.21 pbw stearyl methacrylate, 60.00 pbw of a 50% solution of t-butyl peroctoate in mineral spirits (Lupersol PMS), and 750.00 pbw Orchex 796 oil was added uniformly over 120 minutes. Then the contents of the reactor were held 30 minutes at 100° C. At the end of the hold, the reaction temperature was raised to 120° C. and 260.00 grams of a 10.00 pbw of a 50% solution of t-butyl peroctoate in mineral spirits (Lupersol PMS) and 250.00 pbw Orchex 796 oil was added to the reactor. The reaction was held at 120° C. for 30 minutes. At the end of the 30 minute hold, 6000.00 grams of Orchex 796 oil was added to the batch. The batch was then held at ~120° C. for an additional 30 minute to create a homogeneous solution. The product so formed exhibited a polymer solids content of 32.65 wt %, a viscosity of 38 centistokes at 100° C. (210° F.). Monomer conversion to polymer was calculated to be 98%.

EXAMPLE 2

Preparation of agricultural oil-soluble polymer with grafted polar monomer.

Preparation of Polymer No. 38 (Table 2). A 1 liter reactor was fitted with a thermocouple, a temperature controller, a purge gas inlet, a water-cooled reflux condenser with purge gas outlet, a stirrer, and an addition funnel. To the addition funnel was charged 259.39 grams of a monomer mixture of 230.77 parts by weight (pbw) stearyl methacrylate (97.5% purity), 12.50 pbw dimethylaminopropyl methacrylamide (100% purity), 1.50 pbw of a 50% solution of t-butyl peroctoate in mineral spirits (Lupersol PMS), 2.13 pbw dodecyl mercaptan. Thirty percent (77.82 grams) of the monomer mixture in the addition funnel was charged to the reactor which was then flushed with nitrogen for 30 minutes before applying heat to bring the contents of the reactor to 115° C. When the contents of the reactor reached 115° C., the balance of the monomer mixture in the addition funnel was uniformly charged to the reactor over 60 minutes. At the end of the monomer mixture addition, 38.50 grams of a chaser feed consisting of 1.00 pbw of a 50% solution of t-butyl peroctoate in mineral spirits (Lupersol PMS), and 37.50 pbw Orchex 796 oil was added uniformly over 90 minutes. Thirty minutes into the chaser feed, 12.50 grams of dimethylaminopropyl methacrylamide (100% purity) was charged to the reactor over 15 minutes as a separate feed. At the end of the chaser feed the contents of the reactor were held 60 minutes at 115° C. At the end of the 60 minute hold, 522.94 grams of Orchex 796 oil was added to the batch. The batch was then held at ~115° C. for an additional 30 minute to create a homogeneous solution. The product so formed exhibited a polymer solids content of 28.53 wt %, a viscosity of 22 cSt at 100° C. (210° F.) Monomer conversion to polymer was calculated to be about 95%.

EXAMPLE 3

Preparation of additional agricultural oil-soluble polymers

Additional polymers were prepared according to the method of Example 1. Compositions and physical characteristics are presented in Table 2 below.

TABLE 2

Polymer Compositions and physical characteristics

| Polymer No. | Composition | Monomer Weight % | Mol. wt. | Solids |
|---|---|---|---|---|
| 1 | BehA/DMAPMAm | 90/10 | 29,400 | 27.6 |
| 2 | BehMA/DMAPMAm | 90/10 | 54,500 | 30.8 |
| 3 | SMA/DMAPMAm | 85/15 | 32,800 | 32.7 |
| 4 | CEMA/IDMA/MMA | 28/62/10 | 49,600 | 39.0 |
| 5 | CEMA/IDMA/MMA/DMAPMAm | 25.2/55.8/9/10 | 31,400 | 39.6 |
| 6 | CEMA/IDMA/MMA/DMAPMAm | 26.5/58.9/9.5/5 | 57,900 | 38.2 |
| 7 | CEMA/IDMA/MMA/NVP | 30/56/10/4 | 420,000 | 39.1 |
| 8 | CEMA/LMA/DMAPMAm | 4.5/91.5/4 | 45,900 | |
| 9 | CEMA/LMA/DMAPMAm | 15/65/20 | 35,000 | |
| 10 | CEMA/LMA/IBMA/NVP | 32.7/43.8/13.7/9.8 | 256,000 | 38.6 |
| 11 | IDMA/DMAPMAm | 85/15 | 19,700 | 29.6 |
| 12 | IDMA/MMA | 80/20 | 49,400 | 29.6 |
| 13 | LMA | 100 | 55,200 | 34.0 |
| 14 | LMA/DMAPMAm | 90/10 | 32,700 | 50.0 |
| 15 | LMA/DMAPMAm | 60/40 | 18,700 | 28.1 |
| 16 | LMA/HPMA | 90/10 | 64,800 | 31.5 |
| 17 | LMA/IDMA | 50/50 | 49,100 | 26.8 |
| 18 | LMA/MMA | 86.2/13.2 | 47,900 | 74.0 |
| 19 | LMA/MMA | 90/10 | 47,900 | 74.0 |
| 20 | LMA/NVP | 90/10 | 68,800 | 30.2 |
| 21 | LMA/NVP | 80/20 | 68,000 | 34.8 |
| 22 | SMA/DMAEMA | 95/5 | 49,200 | 29.3 |
| 23 | SMA/DMAEMA | 90/10 | 50,600 | 29.3 |
| 24 | SMA/DMAEMA | 80/20 | 52,300 | 29.1 |
| 25 | SMA/DMAPMAm | 95/5 | 44,400 | 29.4 |
| 26 | SMA/DMAPMAm | 95/5 | 77,700 | 28.7 |
| 27 | SMA/DMAPMAm | 90/10 | 35,300 | 22.7 |
| 28 | SMA/DMAPMAm | 90/10 | 88,200 | 28.0 |
| 29 | SMA/DMAPMAm | 90/10 | 94,000 | 29.3 |
| 30 | SMA/DMAPMAm | 80/20 | 20,600 | 29.6 |
| 31 | SMA/DMAPMAm | 80/20 | 25,600 | 27.9 |
| 32 | SMA/DMAPMAm | 70/30 | 20,000 | 28.9 |
| 33 | SMA/DMAPMAm | 60/40 | 17,600 | 30.2 |
| 34 | SMA/DMAPMAm | 85/15 | 18,600 | 28.8 |
| 35 | SMA/DMAPMAm | 85/15 | 20,800 | 30.3 |
| 36 | SMA/DMAPMAm | 85/15 | 22,000 | 30.0 |
| 37 | SMA/DMAPMAm | 85/15 | 27,600 | 27.9 |
| 38 | SMA/DMAPMAm (5% grafted) | 90/5/5 | 50,600 | 28.5 |
| 39 | SMA/DMAPMAm (toluene) | 90/10 | 27,200 | 51.4 |
| 40 | SMA/IDMA | 50/50 | 56,600 | 30.8 |
| 41 | SMA/IDMA/MMA/HPMA | 30.3/60.7/4/5 | 302,000 | 47.0 |
| 42 | SMA/IDMA/MMA/NVP | 30/56/10/4 | 237,000 | 47.5 |
| 43 | SMA/MVI | 90/10 | 73,900 | 29.4 |
| 44 | BehMA/LMA/DMAPMAm | 48/37/15 | 28,500 | 30.0 |
| 45 | SMA/DMAPMAm | 85/15 | 200,000 | 30.0 |
| 46 | SMA/DMAPMAm | 85/15 | 180,000 | 30.0 |
| 47 | SMA/DMAPMAm | 85/15 | 94,000 | 30.0 |

TABLE 2-continued

Polymer Compositions and physical characteristics

| Polymer No. | Composition | Monomer Weight % | Mol. wt. | Solids |
|---|---|---|---|---|
| 48 | SMA/DMAPMAm | 85/15 | 85,000 | 30.0 |
| 49 | SMA/DMAPMAm | 85/15 | 43,000 | 30.0 |
| 50 | SMA/LMA/NVP | 31.5/58.5/10 | 46,700 | 48.7 |
| 51 | SMA/DMAPMAm | 85/15 | 25,900 | |
| 52 | SMA/LMA/DMAPMAm | 31.5/58.5/10 | 28,600 | |
| 53 | SMA/DMAPMAm | 85/15 | 25,900 | 48.9 |

EXAMPLE 3

Preparation and exaluation of dispersions of pesticides. Compositions tested were typically:

| | |
|---|---|
| Pesticide solids | 50 parts |
| Polymer solids* | 0 to 5.0 parts |
| Orchex 796 oil | 42 to 50 parts |

*provided in oil as 27% to 74% solids

All samples in Table 3 were prepared either at 0%, denoted as "none" for Polymer No. or at 5% by weight of polymer solids, except for experiments with Polymer No. 18 which was incorporated at 2% polymer solids by weight. Polymer was weighed into a tared stainless steel beaker and then Orchex 796 oil was added. The mixture was hand mixed with a spatula. Pesticide was weighed onto weighing paper and slowly added to the polymer/oil mixture with stirring. The mixture was hand mixed thoroughly with a spatula.

Samples too viscous to homogenize directly and dry flowable compositions were pre-dispersed before homogenization. The sample was run until it was a well mixed and flowable mixture.

All samples were homogenized using a a Silverson Model L4R homogenizer. The power dial was slowly increased to ⅔ power. Samples made from technicals and wettable powders were homogenized for 10 minutes. Dry flowables were homogenized until the granules appeared uniformly dispersed. Samples were also mixed during homogenization by gently swirling the sample container. Samples were evaluated as free flowing liquid (reported as "ok") or gelling (reported as "gel").

Bead (Eiger) milling was carried out for for those compositions starting with course particle size pesticides. The 50 ml Eiger mill (Model M50 from Eiger Machinery, Inc.) was loaded with 45 ml of 1 mm glass beads into the bead chamber. Cooling water was turned on. 2.54 cm (one inch) of sample was poured into the sample funnel. The mill was run with the sample mixture for one minute at 3500 rpm. The sample was discharged into a waste container and blown-out to push additional sample from the mill. The remaining sample was added to the sample funnel. The sample was milled for ten to thirty minutes at 3500 rpm. This treatment was believed to be sufficient to provide a dispersion of pesticide having a particle size of 0.5–10 microns. The sample was discharged immediately if there were signs of severe gelling (reported as "gel"). After milling the sample was discharged into a container. Evaluation for successful preparations was based upon examination initially and, if acceptable initially, after one week at 54° C. storage. Testing included:

1) Appearance—Samples were evaluated as free flowing liquid (reported as "ok") or gelling (reported as "gel").

2) Viscosity—The sample was cooled to room temperature. The sample was stirred with a metal spatula for 40 seconds. Viscosity was measured using Brookfield Viscometer LVT, number 3 spindle, and speed setting knob at 60/3. The average of two readings was reported.

3) Storage stability—After one week of storage at 54° C., the sample was removed from the oven and allowed to cool to room temperature. The sample was examined for gelling and separation. If sample separated, the ratio of the top layer to the bottom layer was recorded as percentage separation. A metal spatula was inserted into material and the bottom of the container was probed. The spatula was examined for adhered sticky sediment, and recorded if found. The viscosity of samples that were not badly gelled or separated was measured as above and recorded.

Properties examined:

Initially:

appearance—mixture either liquid or gel; desire no gelling viscosity—desire less than 2000 cps, preferably less than 1000 cps After storage for 2 weeks at 54° C.:

appearance—mixture either liquid or gel; desire no gelling viscosity—desire less than 2000 cps, preferably less than 1000 cps % separation—top clear liquid separation; desire less than 10%.

sedimentation—sticky sediment on the bottom of jar; desire none.

Results were classified by the following key words, which are listed in order of decreasing performance:

ok=Liquid, <1000 cps viscosity, <10% sep, no sediment sep=Separation greater than 10% after storage.

visc1=Viscosity above 1000 cps before storage.

visc2=Viscosity above 1000 cps after storage.

sed=Sedimentation severe enough to affect viscosity. movement to pass)

bead=gels during or after bead milling (sample must have fluid movement to pass)

gel=Immediately or after homogenization (sample must have fluid pass)

Oil suspensions that exhibit gelling in the homogenizer or bead mill are not acceptable. All others are acceptable, but in varying degrees of quality.

TABLE 3

Testing of Polymer Dispersions

| Sample ID | Active Ingredient | Polymer No. | Homogenizer | Bead Mill | Appearance | Viscosity | Appearance | Visc. | % Sep | Sed |
|---|---|---|---|---|---|---|---|---|---|---|
| Comp Da | Dithane M 45-T | none | gel | n/a | n/a | n/a | n/a | n/a | n/a | n/a |
| D-1 | Dithane M 45-T | 4 | ok | ok | ok | 330 | ok | 220 | 3 | none |
| D-2 | Dithane M 45-T | 18 | ok | ok | ok | 270 | ok | 300 | 2 | none |
| Comp Db | Dithane M 45-T | 12 | ok | gel | gel | n/a | n/a | n/a | n/a | n/a |
| Comp Dc | Dithane M 45-T | 15 | gel | n/a | n/a | n/a | n/a | n/a | n/a | n/a |
| D-3 | Dithane M 45-T | 32 | ok | ok | ok | 380 | ok | 350 | 1 | none |
| D-4 | Dithane M 45-T | 9 | ok | ok | ok | 320 | sep | n/a | 5 | yes |
| D-5 | Dithane M 45-T | 31 | ok | ok | ok | 240 | ok | 320 | 2 | none |
| D-6 | Dithane M 45-T | 36 | ok | ok | ok | 310 | ok | 450 | 2 | none |
| D-7 | Dithane M 45-T | 37 | ok | ok | ok | 350 | ok | 300 | 2 | none |
| D-8 | Dithane M 45-T | 29 | ok | ok | ok | 810 | ok | 730 | 1 | none |
| D-9 | Dithane M 45-T | 28 | ok | ok | ok | 790 | ok | 1300 | 1 | none |
| D-10 | Dithane M 45-T | 44 | ok | ok | ok | 130 | ok | n/a | 0 | yes |
| Comp Dd | Dithane M 45-T | 45 | ok | ok | ok | 690 | gel | n/a | 2 | no |
| Comp De | Dithane M 45-T | 46 | ok | ok | ok | 540 | ok | 1880 | 2 | no |
| D-13 | Dithane M 45-T | 47 | ok | ok | ok | 510 | ok | 860 | 5 | no |
| D-14 | Dithane M 45-T | 48 | ok | ok | ok | 410 | ok | 630 | 2 | slight |
| D-15 | Dithane M 45-T | 49 | ok | ok | ok | 300 | ok | 240 | 2 | slight |
| D-16 | Dithane M 45-T | 38 | ok | ok | ok | 230 | ok | 230 | 3 | none |
| D-17 | Dithane M 45-T | 21 | ok | ok | ok | 620 | ok | 845 | 2 | none |
| D-18 | Dithane M 45-T | 20 | ok | ok | ok | 370 | ok | 190 | 2 | none |
| D-19 | Dithane M 45-T | 23 | ok | ok | ok | 260 | ok | 250 | 2 | none |
| D-20 | Dithane M 45-T | 41 | ok | ok | ok | 590 | ok | 440 | 1 | none |
| D-21 | Dithane M 45-T | 43 | ok | gel | gel | n/a | n/a | n/a | n/a | n/a |
| Comp Ga | Gallery75df | none | gel | n/a | gel | n/a | n/a | n/a | n/a | n/a |
| Comp Gb | Gallery75df | 18 | ok | n/a | ok | 780 | gel | n/a | 0 | none |
| G-1 | Gallery75df | 36 | ok | n/a | ok | 430 | gel | n/a | 50 | yes |
| G-2 | Gallery75df | 28 | ok | n/a | ok | 540 | ok | 720 | 2 | none |
| G-3 | Gallery75df | 25 | ok | n/a | ok | 390 | ok | 1250 | 1 | none |
| Comp 1a | Imidan70wp | none | gel | n/a | gel | n/a | n/a | n/a | n/a | n/a |
| Comp 1b | Imidan70wp | 18 | gel | n/a | gel | n/a | n/a | n/a | n/a | n/a |
| Comp 1c | Imidan70wp | 12 | gel | n/a | gel | n/a | n/a | n/a | n/a | n/a |
| I-1 | Imidan70wp | 15 | ok | n/a | ok | 1200 | gel | n/a | 1 | none |
| I-2 | Imidan70wp | 36 | ok | n/a | ok | 300 | sep | n/a | 25 | yes |
| I-3 | Imidan70wp | 28 | ok | n/a | ok | 500 | sep | 900 | 5 | none |
| I-4 | Imidan70wp | 25 | ok | n/a | ok | 340 | sep | 470 | 2 | none |
| I-5 | Imidan70wp | 23 | ok | n/a | ok | 290 | sep | 350 | 5 | none |
| I-6 | Imidan70wp | 43 | ok | n/a | ok | 500 | sep | n/a | 33 | yes |
| Comp Ka | Kerb50w | none | gel | n/a | n/a | n/a | n/a | n/a | n/a | n/a |
| Comp Kb | Kerb50w | 4 | gel | n/a | gel | n/a | n/a | n/a | n/a | n/a |
| Comp Kc | Kerb50w | 18 | gel | n/a | gel | n/a | n/a | n/a | n/a | n/a |
| Comp | Kerb50w | 12 | gel | n/a | gel | n/a | n/a | n/a | n/a | n/a |

TABLE 3-continued

Testing of Polymer Dispersions

| Sample ID | Active Ingredient | Polymer No. | Homogenizer | Bead Mill | Appearance | Viscosity | Appearance | Visc. | % Sep | Sed |
|---|---|---|---|---|---|---|---|---|---|---|
| Comp Kd Ke | Kerb50w | 15 | ok | n/a | ok | 630 | sep | 650 | 7 | none |
| K-1 | Kerb50w | 36 | ok | n/a | ok | 240 | sep | 320 | 10 | none |
| K-2 | Kerb50w | 28 | ok | n/a | ok | 260 | sep | 340 | 7 | none |
| K-3 | Kerb50w | 25 | ok | n/a | ok | 420 | ok | 630 | 0 | none |
| K-4 | Kerb50w | 23 | ok | n/a | ok | 1040 | ok | 1600 | 0 | none |
| K-5 | Kerb50w | 43 | ok | n/a | ok | 580 | ok | 820 | 0 | none |
| Comp IWPa | IndarWP75 | none | gel | n/a | n/a | n/a | n/a | n/a | n/a | n/a |
| Comp IWPb | IndarWP75 | 12 | gel | n/a | n/a | n/a | n/a | n/a | n/a | n/a |
| Comp IWPc | IndarWP75 | 18 | gel | n/a | n/a | n/a | n/a | n/a | n/a | n/a |
| IWP-1 | IndarWP75 | 23 | ok | n/a | ok | 510 | gel | n/a | none | none |
| IWP-2 | IndarWP75 | 31 | ok | n/a | ok | 520 | ok | 900 | 2 | none |
| IWP-3 | IndarWP75 | 36 | ok | n/a | ok | 450 | ok | 980 | 2 | none |
| IWP-4 | IndarWP75 | 43 | ok | n/a | ok | 690 | gel | n/a | n/a | n/a |
| Comp Ia | Indar tech | none | ok | gel | gel | n/a | n/a | n/a | n/a | n/a |
| Comp Ib | Indar tech | 40 | ok | gel | gel | n/a | n/a | n/a | n/a | n/a |
| Comp Ic | Indar tech | 12 | ok | gel | gel | n/a | n/a | n/a | n/a | n/a |
| Comp Id | Indar tech | 15 | ok | gel | gel | n/a | n/a | n/a | n/a | n/a |
| I-1 | Indar tech | 31 | ok | ok | ok | 520 | ok | 670 | none | none |
| I-2 | Indar tech | 30 | ok | ok | ok | 620 | ok | 620 | none | none |
| I-3 | Indar tech | 44 | ok | ok | ok | 650 | ok | 1100 | 0 | none |
| Comp Ie | Indar tech | 45 | ok | ok | ok | 780 | ok | 520 | 0 | none |
| Comp If | Indar tech | 46 | ok | ok | ok | 760 | ok | 620 | 0 | none |
| I-4 | Indar tech | 47 | ok | ok | ok | 600 | ok | 500 | 0 | none |
| I-5 | Indar tech | 48 | ok | ok | ok | 550 | ok | 380 | 0 | none |
| I-6 | Indar tech | 49 | ok | ok | ok | 480 | ok | 360 | 0 | none |
| I-7 | Indar tech | 36 | ok | ok | ok | 350 | ok | 515 | none | none |
| I-8 | Indar tech | 11 | ok | gel | gel | n/a | n/a | n/a | n/a | n/a |
| I-9 | Indar tech | 1 | ok | gel | gel | n/a | n/a | n/a | n/a | n/a |
| I-10 | Indar tech | 2 | ok | ok | ok | 1500 | gel | n/a | none | none |
| I-11 | Indar tech | 5 | ok | gel | gel | n/a | n/a | n/a | n/a | n/a |
| I-12 | Indar tech | 27 | ok | ok | ok | 650 | gel | n/a | none | none |
| I-13 | indar tech | 29 | ok | ok | ok | 680 | ok | 620 | none | none |
| I-14 | Indar tech | 28 | ok | ok | ok | 600 | ok | 490 | none | none |
| I-15 | Indar tech | 39 | ok | ok | ok | 790 | gel | n/a | none | none |
| I-16 | Indar tech | 14 | ok | ok | ok | 1520 | gel | n/a | none | none |
| I-17 | Indar tech | 26 | ok | ok | ok | 960 | gel | n/a | none | none |
| I-18 | Indar tech | 38 | ok | gel | gel | n/a | n/a | n/a | n/a | n/a |
| I-19 | Indar tech | 20 | ok | ok | gel | n/a | n/a | n/a | n/a | n/a |
| I-20 | Indar tech | 24 | ok | ok | ok | 1680 | gel | n/a | none | none |
| I-21 | Indar tech | 43 | ok | ok | ok | 580 | ok | 800 | none | none |
| Comp SWPa | Systhane 40wp | 4 | gel | n/a | gel | n/a | n/a | n/a | n/a | n/a |
| Comp | Systhane | 18 | gel | n/a | gel | n/a | n/a | n/a | n/a | n/a |

TABLE 3-continued

Testing of Polymer Dispersions

| Sample ID | Active Ingredient | Polymer No. | Homo-genizer | Bead Mill | Appear-ance | Viscosity | Appear-ance | Visc. | % Sep | Sed |
|---|---|---|---|---|---|---|---|---|---|---|
| SWPb | 40wp | | | | | | | | | |
| Comp SWPc | Systhane 40wp | 12 | gel | n/a | n/a | n/a | n/a | n/a | n/a | n/a |
| SWP-1 | Systhane 40wp | 31 | ok | n/a | ok | 470 | ok | 370 | 3% | none |
| SWP-2 | Systhane 40wp | 1 | gel | n/a | gel | n/a | n/a | n/a | n/a | n/a |
| SWP-3 | Systhane 40wp | 36 | ok | n/a | ok | 530 | ok | 390 | 3 | none |
| SWP-4 | Systhane 40wp | 29 | ok | n/a | ok | 1010 | ok | 1700 | none | none |
| SWP-5 | Systhane 40wp | 44 | ok | n/a | ok | 390 | ok | 380 | 0 | none |
| Comp SWPd | Systhane 40wp | 45 | ok | n/a | ok | 980 | ok | 1670 | 0 | none |
| Comp SWPe | Systhane 40wp | 46 | ok | n/a | ok | 840 | ok | 1700 | 0 | none |
| SWP-6 | Systhane 40wp | 47 | ok | n/a | ok | 550 | ok | 1460 | 0 | none |
| SWP-7 | Systhane 40wp | 48 | ok | n/a | ok | 600 | ok | n/a | n/a | n/a |
| SWP-8 | Systhane 40wp | 49 | ok | n/a | ok | 220 | sep | 300 | 20 | none |
| SWP-9 | Systhane 40wp | 25 | ok | n/a | ok | 630 | ok | 690 | 0 | none |
| SWP-9 | Systhane 40wp | 23 | gel | n/a | n/a | n/a | n/a | n/a | n/a | n/a |
| SWP-10 | Systhane 40wp | 7 | gel | n/a | gel | n/a | n/a | n/a | n/a | n/a |
| SWP-11 | Systhane 40wp | 43 | ok | n/a | ok | 790 | ok | 790 | none | none |
| Comp TCa | T-chloro-thalonil | none | ok | gel | gel | n/a | n/a | n/a | n/a | n/a |
| Comp TCb | T-chloro-thalonil | 4 | ok | gel | gel | n/a | n/a | n/a | n/a | n/a |
| Comp TCc | T-chloro-thalonil | 18 | ok | gel | gel | n/a | n/a | n/a | n/a | n/a |
| Comp TCd | T-chloro-thalonil | 12 | ok | gel | gel | n/a | n/a | n/a | n/a | n/a |
| Comp TCe | T-chloro-thalonil | 15 | ok | gel | gel | n/a | n/a | n/a | n/a | n/a |
| TC-1 | T-chloro-thalonil | 31 | ok | ok | ok | 160 | sep | n/a | 0 | yes |
| TC-2 | T-chloro-thalonil | 36 | ok | ok | ok | 160 | sep | n/a | 0 | yes |
| TC-3 | T-chloro-thalonil | 28 | ok | ok | ok | 250 | sep | n/a | 0 | yes |
| TC-4 | T-chloro-thalonil | 25 | ok | ok | ok | 240 | ok | 170 | 0 | none |
| TC-5 | T-chloro-thalonil | 23 | ok | ok | ok | 340 | ok | 180 | 0 | none |
| TC-6 | T-chloro-thalonil | 20 | ok | gel | gel | n/a | n/a | n/a | n/a | n/a |
| TC-7 | T-chloro-thalonil | 43 | ok | ok | ok | 80 | gel | n/a | 0 | none |
| Comp Ta | Thifluz-amide | none | gel | n/a | gel | n/a | n/a | n/a | n/a | n/a |
| Comp Tb | Thifluz-amide | 18 | get | n/a | gel | n/a | n/a | n/a | n/a | n/a |
| Comp Tc | Thifluz-amide | 4 | gel | n/a | gel | n/a | n/a | n/a | n/a | n/a |
| Comp Td | Thifluz-amide | 12 | gel | n/a | gel | n/a | n/a | n/a | n/a | n/a |
| Comp Te | Thifluz-amide | 15 | gel | n/a | gel | n/a | n/a | n/a | n/a | n/a |
| T-1 | Thifluz-amide | 36 | ok | n/a | ok | 560 | ok | 985 | 1 | none |
| T-2 | Thifluz-amide | 28 | ok | n/a | ok | 820 | ok | 1530 | 2 | none |
| T-3 | Thifluz-amide | 25 | ok | n/a | ok | 790 | ok | 1150 | 2 | none |
| T-4 | Thifluz-amide | 22 | gel | n/a | gel | n/a | n/a | n/a | n/a | n/a |
| T-5 | Thifluz-amide | 43 | gel | n/a | gel | n/a | n/a | n/a | n/a | n/a |

TABLE 3-continued

Testing of Polymer Dispersions

| Sample ID | Active Ingredient | Polymer No. | Homo-genizer | Bead Mill | Appear-ance | Viscosity | Appear-ance | Visc. | % Sep | Sed |
|---|---|---|---|---|---|---|---|---|---|---|
| | amide | | | | | | | | | |
| Comp Va | Visor50w | none | gel | n/a | n/a | n/a | n/a | n/a | n/a | n/a |
| Comp Vb | Visor50w | 4 | gel | n/a | n/a | n/a | n/a | n/a | n/a | n/a |
| Comp Vc | Visor50w | 18 | gel | n/a | n/a | n/a | n/a | n/a | n/a | n/a |
| Comp Vd | Visor50w | 12 | gel | n/a | n/a | n/a | n/a | n/a | n/a | n/a |
| Comp Ve | Visor50w | 15 | gel | n/a | n/a | n/a | n/a | n/a | n/a | n/a |
| V-1 | Visor50w | 44 | ok | n/a | ok | 400 | ok | n/a | 2 | none |
| Comp Vf | Visor50w | 45 | ok | n/a | ok | 860 | gel | n/a | 1 | none |
| Comp Vg | Visor50w | 46 | ok | n/a | ok | 820 | gel | n/a | 1 | none |
| V-2 | Visor50w | 47 | ok | n/a | ok | 600 | gel | n/a | 1 | none |
| V-3 | Visor50w | 48 | ok | n/a | ok | 580 | gel | n/a | 1 | n/a |
| V-4 | Visor50w | 49 | ok | n/a | ok | 1400 | gel | n/a | 1 | none |
| V-5 | Visor50w | 36 | ok | n/a | ok | 580 | ok | 480 | 4 | none |
| V-6 | Visor50w | 28 | ok | n/a | ok | 570 | ok | 1100 | 2 | none |
| V-7 | Visor50w | 25 | ok | n/a | ok | 380 | ok | 660 | 0 | none |
| V-8 | Visor50w | 23 | gel | n/a | n/a | n/a | n/a | n/a | n/a | n/a |
| V-9 | Visor50w | 43 | gel | n/a | n/a | n/a | n/a | n/a | n/a | n/a |

EXAMPLE 4

Preparation and evaluation of Goal (oxyfluorfen) oil dispersion

10% Polymer No. 50, 42% Goal 95 Technical, 43% 100 neutral oil, and 5% Latron CS-7 (adjuvant-surfactant; from Rohm and Haas Company) were homogenized together and then Eiger milled for 30 minutes. A satisfactory dispersion was produced.

EXAMPLE 5

Preparation and evaluation of Goal/Glyphosate oil dispersion

A mixture of 3.35% of Goal (oil flowable), 53.65% Glyphosate, 3.5% Polymer No. 51, 34.5% 100N neutral oil and 5% Triton X-114 were weighed into a ceramic jar. Quarter inch ceramic milling media was then added to the ceramic jar. The ceramic jar was placed on a roller and ball milled at 40 rpm for seventy hours. A satisfactory dispersion was produced.

EXAMPLE 6

Preparation and evaluation of RH 7281 dispersion

A mixture of 40% RH7281 benzamide, 3% Polymer No. 52, and 57% 100 N neutral oil were blended together, homogenized and Eiger milled according to the method of Example 3. A sample of the composition was stored in the laboratory at ambient temperature for seven months and appeared uniform with no separation.

EXAMPLE 7

Preparation and evaluation of glyphosate dispersion

A sample of glyphosate isopropyl ammonium salt was jet air milled to a particle size of 2–5 microns. A sample of 45.0 g the glyphosate isopropyl ammonium salt, 3.5 g. Polymer No. 53, and 47.85 Chevron 100 neutral oil were mixed in a beaker and homogenized in a beaker for 2–3 minutes using a Ultra-Turrax T25 homogenizer (made by Janke & Kunke). The product dispersion was acceptable; it was a free-flowing off-white fluid with no gelling. Viscosity was 303 cps at 25° C. (Brookfield viscometer, Spindle #1, 100 rpm).

EXAMPLE 8

Preparation and evaluation of Dithane/cymoxanil dispersion

A mixture of 50 parts of Dithane technical grade (86% a.i.), 6 parts of cymoxanil (95% a.i.), and 5 parts Polymer sample No. 36 made up to 100 parts with Orchex 796 oil was prepared. The mixture was homogenized for 5 minutes and bead milled for 5 minutes. A uniform dispersion with a viscosity of 2000 cps resulted. After one week at 40° C. the dispersion had a viscosity of 2500 cps.

EXAMPLE 9

Preparation and evaluation of Dithane/copper hydroxide dispersion

A mixture of 30 parts of Dithane technical grade (86% a.i.), 28 parts of copper hydroxide (65% copper) and 5 parts Polymer sample No. 36 made up to 100 parts with Orchex 796 oil was prepared. The mixture was homogenized for 5 minutes and bead milled for 5 minutes. A uniform dispersion with a viscosity of 1500 cps resulted. After one week at 40° C. the dispersion had a viscosity of 1700 cps.

We claim:

1. A stable dispersion of a pesticide in an agricultural oil comprising; a pesticide having a particle size from 0.5–10 microns and selected from the group consisting of chlorinated nitrile, triazole, aralkyl triazole, triazole anilide, benzamide, alkyl benzamide, diphenyl ether, pyridine carboxylic acid, chloroaniline, organophosphate, phosphonic glycine salt, and mixtures thereof; an agricultural oil; and an agricultural oil-soluble polymor, said polymer having a weight average molecular weight from 3,000 to 120,000 and comprising 65 to 97.5% by weight of an alkyl acrylate, alkyl methacrylato, or mixture thereof, wherein the alkyl group contains an average of at least seven carbon atoms, and 2.5 to 35% by weight of a copolymerized polar monomer.

2. The dispersion of claim 1 wherein said pesticide is selected from the group consisting of chlorothalonil, myclobutanil, fenbuconazole, thifluzamide, isoxaben, propyzamide, thiazopyr, oxyfluorfen, glyphosate isopropyl ammonium salt, propanil, phosmet, and mixtures thereof.

3. The dispersion of claim 1 wherein said polymer has a weight average molecular weight from 20,000 to 75,000.

4. The dispersion of claim 1 wherein said polymer comprises 10–20% by weight of said copolymerized polar monomer.

5. The dispersion of claim 1 wherein said polymer is a copolymer comprising 85–90% by weight $C_{12}$–$C_{20}$ methacrylate and 10–20% dimethylaminopropyl methacrylamide.

6. A stable dispersion of a pesticide in an agricultural oil comprising: ethylene bisdithiocarbamate having a particle size from 2–10 microns; an agricultural oil; and an agricultural oil-soluble polymer, said polymer having a weight average molecular weight from 3,000 to 90,000 and comprising 65 to 100% by weight of an alkyl acrylate, alkyl methacrylate, or mixture thereof, wherein the alkyl group contains an average of at least seven carbon atoms, aud 0 to 35% by weight of a copolymerized polar monomer.

7. A method for forming ti stable dispersion of a pesticide in an agricultural oil comprising admixing a pesticide selected from the group consisting of chlorinated nitrile, triazole, aralkyl triazole, triazole anilide, benzamide. alkyl benzamide, diphenyl ether, pyridine carboxylic acid, chloroaniline, organophosphate, phosphonic glycine salt; an agricultural oil; and an agricultural oil-soluble polymer, said polymer having a weight average molecular weight from 3,000 to 120,000 and comprising 65 to 97.5% by weight of an alkyl acrylate, alkyl methacrylate, or mixture thereof, wherein the alkyl group contains an average of at least seven carbon atoms, and 2.5 to 35% by weight of a copolymerized polar monomor and mixing or shearing said admixture until said pesticide has a particle size from 0.5 to 10 microns.

8. A method for forming a stable dispersion of A pesticide in an agricultural oil comprising admixing ethylene bisdithiocarbamate; an agricultural oil; and an agricultural oil-soluble polymer, said polymer having a weight average molecular weight from 8,000 to 90,000 and comprising 65 to 100% by weight of an alkyl acrylate, alkyl methacrylate, or mixture thereof, wherein the alkyl group contains an average of at least seven carbon atoms, and 0 to 35% by weight of a copolymerized polar monomer and mixing or shearing said admixture until said ethylene bisdithiocarbamate has a particle size from 2 to 10 microns.

* * * * *